United States Patent
Yumoto et al.

(10) Patent No.: US 8,841,113 B2
(45) Date of Patent: Sep. 23, 2014

(54) ALKALIPHILIC LACTIC ACID BACTERIUM

(75) Inventors: Isao Yumoto, Sapporo (JP); Kazuaki Yoshimune, Sapporo (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 127 days.

(21) Appl. No.: 13/503,064

(22) PCT Filed: Oct. 22, 2010

(86) PCT No.: PCT/JP2010/068726
§ 371 (c)(1),
(2), (4) Date: Apr. 20, 2012

(87) PCT Pub. No.: WO2011/049205
PCT Pub. Date: Apr. 28, 2011

(65) Prior Publication Data
US 2012/0202254 A1    Aug. 9, 2012

(30) Foreign Application Priority Data

Oct. 23, 2009  (JP) ................................ 2009-244894

(51) Int. Cl.
*C12N 1/20* (2006.01)
*C12P 7/56* (2006.01)
*C12R 1/46* (2006.01)

(52) U.S. Cl.
CPC .............. *C12P 7/56* (2013.01); *C12P 2203/00* (2013.01); *C12R 1/46* (2013.01); *C12P 2201/00* (2013.01)
USPC ...................................... 435/252.3; 435/139

(58) Field of Classification Search
USPC ..................................................... 435/252.3
See application file for complete search history.

(56) References Cited

FOREIGN PATENT DOCUMENTS

| JP | 63-167796 A | 7/1988 |
| JP | 2000-245491 A | 9/2000 |
| JP | 2005-073549 A | 3/2005 |
| JP | 2009-125050 A | 6/2009 |

OTHER PUBLICATIONS

Patel et al., GenBank accession No. NR_041704, 2011.*
Stackebrandt, E., Encyclopedia of Life Sciences, pp. 1-7, 2001.*
Taniguchi, M., et al., "Production of L-lactic acid from a mixture of xylose and glucose by co-cultivation of lactic acid bacteria", Appl Microbiol Biotechnol, Dec. 2004, vol. 66(2), pp. 160-165.
Hiroto Yokaryo., et al., "Lactic acid production by alkaliphilic microorganisms isolated from semi-tropical region (Okinawa)", Abstracts of the Annual Meeting of the Society for Biotechnology, Japan, vol. 61st, p. 121, 11p23, Aug. 25, 2009.
Morio Ishikawa, "Koensei Ko-Alkali-sei Nyusankin no Tayosei to Tokusei", Jpn. J. Food Microbiol., vol. 26(2), pp. 49 to 59, Jul. 31, 2009.
Ludwig, et al., "Family IV. Enterococcaceae fam. nov.", Bergey's Manual of Systematic Biology, Second Ed., vol. 3, Sep. 15, 2009, Springer, New York, NY, pp. 594-607.
Hideshi Yanase, et al., Pyruvate Production by Enteroccus *Casseliflavus* . . . , Journal of Fermentation and Bioengineering, vol. 73, No. 4, pp. 287-291, 1992.
Christopher P. McHugh, DMD, et al., PH Required to Kill *Enterococcus* . . . , Journal of Endodontists, vol. 30, No. 4, 2004.
Miyuki Kawano, et al., Potassium Uptake With Low Affinity and High Rate . . . , Arch. Microbiol, 175, pp. 41-45, 2001.
Database DDBJ/EMBL/GenBank [online], Accession No. FJ357239, http://www.ncbi.nlm.nih.gov/nuccore/209972505?sat=4&satkey=25924183>Nov. 1, 2008 updated, [retrieved on Nov. 27, 2013], Definition: *Enterococcus casseliflavus* strain MMBI 16S ribosomal RNA gene, partial sequence).
Database DDBJ/EMBL/GenBank [online], Accession No. EU887827, http://www.ncbi.nlm.nih.gov/nuccore/195933884?sat=13&satkey=9422486>Aug. 11, 2008 updated, [retrieved on Nov. 27, 2013], Definition: *Enterococcus faecalis* strain H13 16S ribosomal RNA gene, partial sequence).
Database DDBJ/EMBL/GenBank [online], Accession No. AB362598, http://www.ncbi.nlm.nih.gov/nuccore/157907330?sat=3&satkey=7261460>Oct. 4, 2007 updated, [retrieved on Nov. 27, 2013], Definition: *Enterococcus hirae* gene for 16S rRNA, partial sequence, strain: NRIC 01 09).

* cited by examiner

*Primary Examiner* — Delia Ramirez
(74) *Attorney, Agent, or Firm* — Lucas & Mercanti, LLP

(57) ABSTRACT

The present invention relates to a method for producing lactic acid from plant biomass without requiring sterilization, and specifically relates to a method for producing lactic acid comprising culturing alkaliphilic lactic acid bacteria under non-sterile condition and at a pH of 9 to 11 in a medium containing a cellulose glycosylation solution and then further culturing the bacteria at a pH of 5 to 9.

7 Claims, 4 Drawing Sheets

SEQUENCE LISTING

```
<160> NUMBER OF SEQ ID NOS: 1

<210> SEQ ID NO 1
<211> LENGTH: 1245
<212> TYPE: DNA
<213> ORGANISM: Enterococcus casseliflavus

<400> SEQUENCE: 1
gagtggcgaa cgggtgagta acacgtgggt aacctgccca tcagaagggg ataacacttg      60
gaaacaggtg ctaataccgt ataacactat tttccgcatg gaagaaagtt gaaaggcgct     120
tttgcgtcac tgatggatgg acccgcggtg cattagctag ttggtgaggt aacggctcac     180
caaggcaacg atgcatagcc gacctgagag ggtgatcggc cacactggga ctgagacacg     240
gcccagactc ctacgggagg cagcagtagg gaatcttcgg caatggacga aagtctgacc     300
gagcaacgcc gcgtgagtga agaaggtttt cggatcgtaa aactctgttg ttagagaaga     360
acaaggatga gagtaaaatg ttcatccctt gacggtatct aaccagaaag ccacggctaa     420
ctacgtgcca gcagccgcgg taatacgtag gtggcaagcg ttgtccggat ttattgggcg     480
taaagcgagc gcaggcggtt tcttaagtct gatgtgaaag cccccggctc aaccggggag     540
ggtcattgga aactgggaga cttgagtgca gaagaggaga gtggaattcc atgtgtagcg     600
gtgaaatgcg tagatatatg gaggaacccc agtggcgaag gcggctctct ggtctgtaac     660
tgacgctgag gctcgaaagc gtggggagcg aacaggatta gataccctgg tagtccacgc     720
cgtaaacgat gagtgctaag tgttggaggg tttccgccct tcagtgctgc agcaaacgca     780
ttaagcactc cgcctgggga gtacgaccgc aaggttgaaa ctcaaaggaa ttgacggggg     840
cccgcacaag cggtggagca tgtggtttaa ttcgaagcaa cgcgaagaac cttaccaggt     900
cttgacatcc tttgaccact ctagagatag agcttcccct tcgggggcaa agtgacaggt     960
ggtgcatggt tgtcgtcagc tcgtgtcgtg agatgttggg ttaagtcccg caacgagcgc    1020
aacccttatt gttagttgcc atcatttagt tgggcactct agcgagactg ccggtgacaa    1080
accggaggaa ggtggggatg acgtcaaatc atcatgcccc ttatgacctg ggctacacac    1140
gtgctacaat gggaagtaca acgagttgcg aagtcgcgag gctaagctaa tctcttaaag    1200
cttctctcag ttcggattgt aggctgcaac tcgcctacat gaagc                    1245
```

ALKALIPHILIC LACTIC ACID BACTERIUM

CROSS-REFERENCE TO RELATED APPLICATIONS

This application is a 371 of PCT/JP2010/068726, filed Oct. 22, 2010, which claims the benefit of Japanese Patent Application No. 2009-244894, filed Oct. 23, 2009, the contents of each of which are incorporated herein by reference.

TECHNICAL FIELD

The present invention relates to a novel alkaliphilic lactic acid bacterium and a method for producing lactic acid by non-sterile fermentation, for example.

BACKGROUND ART

Polylactic acid is an eco-friendly biodegradable plastic, which is produced with the use of lactic acid as a raw material. To improve the quality of polylactic acid, L-isomer or D-isomer of lactic acid with high optical purity is required. In this regard, lactic acid obtained by fermentation is more advantageous than lactic acid synthesized from petroleum, because of its high optical purity.

Depletion of oil resources is predicted to occur in the future. Substitution of petroleum-derived plastic with polylactic acid will be required. However, polylactic acid is more expensive than petroleum-derived plastic, and thus further reduction in lactic fermentation cost is required.

In general, lactic fermentation is performed using food plant biomass such as corn (maize) as a carbon source, and thus lactic acid production with the (easy) use of a food resource as a raw material causes rising food prices. Accordingly, development of a lactic fermentation technique with the use of nonfood plant biomass that does not compete with foods is also desired.

Typical known examples of nonfood plant biomass include non-edible parts of rice and oats, such as rice straw and wheat straw. Rice straw is disposed by open burning or being plowed into agricultural fields, but disposal differs depending on area. Rice straw is an unused resource, with only about a half thereof is used. However, cellulase for glycosylation of rice straw is expensive, and thus rice straw is not easily used.

Hydrolysis using concentrated sulfuric acid is employed for glycosylation of woody biomass. However, this method is problematic in terms of neutralization cost after treatment with concentrated sulfuric acid, also because it increases environmental burdens due to the use of concentrated sulfuric acid. Furthermore, the method requires purification of glucose from a solution treated with concentrated sulfuric acid, causing a further increase in cost.

Known lactic fermentation involves performing 20 minutes of sterilization at 120° C. for medium before inoculation of lactic acid bacteria. This sterilization not only requires expensive equipment such as a boiler for a culture apparatus, but also results in a large cost for sterilization. Furthermore, pressure is applied for sterilization, and thus a firm container is required, which leads to high initial cost.

Meanwhile, other known lactic fermentation techniques using plant biomass as a raw material are implemented with an open system that involves no sterilization (patent documents 1 and 2). With a technique that involves inoculation of large amounts of lactic acid bacteria (patent document 1), about 2.5% L-lactic acid can be obtained per culture solution within 3 days. Also, with a lactic fermentation technique (patent document 2) implemented at a high temperature of about 45° C., about 4% L-lactic acid can be obtained per culture solution within 2 days.

However, a method that involves inoculation of large amounts of lactic acid bacteria requires culturing large amounts of cells upon lactic fermentation, resulting in much cost and labor. However, lactic fermentation at a high temperature (about 45° C.) requires expenditures for maintaining a fermentation tank at such temperature. Furthermore, these lactic fermentation techniques have drawbacks in that only about up to 4% lactic acid is obtained per culture solution, resulting in a high cost for lactic acid purification following fermentation.

Therefore, a method required herein is to perform lactic fermentation from plant biomass at room temperature with small amounts of bacteria to be inoculated and without performing sterilization.

PRIOR ART DOCUMENTS

Patent Documents

Patent document 1 JP Patent Publication (Kokai) No. 2000-245491 A
Patent document 2 JP Patent Publication (Kokai) No. 2005-73549 A

SUMMARY OF THE INVENTION

Problems to be Solved by the Invention

In view of the above circumstances, an object of the present invention is to provide a method for producing lactic acid from plant biomass without requiring sterilization, for example.

Means for Solving the Problems

As a result of intensive studies to achieve the above object, the present inventors have isolated an alkaliphilic lactic acid bacterium capable of generating high-concentration lactic acid from rice straw-derived glucose, found that high-concentration lactic acid can be produced from a glycosylation solution derived from unsterilized non-edible plant part biomass with the use of the alkaliphilic lactic acid bacterium, and thus completed the present invention.

The present invention encompasses the following (1) to (16).

(1) An alkaliphilic lactic acid bacterium belonging to the genus *Enterococcus*, which has a 16S ribosomal RNA gene consisting of the nucleotide sequence represented by SEQ ID NO: 1 or having 95% or more homology with the nucleotide sequence represented by SEQ ID NO: 1, and which grows under alkaline conditions of pH 10 or more.

(2) The alkaliphilic lactic acid bacterium according to (1), which is *Enterococcus casseliflavus*.

(3) The alkaliphilic lactic acid bacterium according to (1) or (2), which is a microorganism specified with accession No. FERM BP-11295.

(4) A method for producing lactic acid comprising a step of culturing the alkaliphilic lactic acid bacterium according to any one of (1) to (3) under non-sterile condition and at a pH of 9 to 11 in a medium containing a cellulose glycosylation solution and further culturing the bacterium at a pH of 5 to 9.

(5) The method according to (4), wherein the cellulose glycosylation solution is obtained from a non-edible plant part.

(6) The method according to (5), wherein the non-edible plant part is rice straw, wheat straw, or maize stem.
(7) The method according to any one of (4) to (6) comprising a step of soaking plant biomass in an alkali solution to remove lignin and a step of bringing cellulose fiber into contact with cellulase to obtain a cellulose glycosylation solution.
(8) The method according to (7), wherein the alkali solution is a caustic soda solution.
(9) The method according to (7) or (8) comprising leaving the soaked plant biomass at room temperature or subjecting the soaked plant biomass to heat treatment.
(10) A method for generating glucose comprising a step of soaking plant biomass in an alkali solution to remove lignin and a step of bringing cellulose fiber into contact with cellulase.
(11) The method according to (10), wherein the plant biomass is a non-edible plant part.
(12) The method according to (11), wherein the non-edible plant part is rice straw, wheat straw, or maize stem.
(13) The method according to any one of (10) to (12), wherein the alkali solution is a caustic soda solution.
(14) The method according to any one of (10) to (13) comprising leaving the soaked plant biomass at room temperature or subjecting the soaked plant biomass to heat treatment.
(15) A composition for lactic fermentation containing glucose obtained by the method according to any one of (10) to (14).
(16) The composition for lactic fermentation according to (15) containing bean curd refuse.

This description includes part or all of the contents as disclosed in the description and/or drawings of Japanese Patent Application No. 2009-244894, which is a priority document of the present application.

Effects of the Invention

According to the present invention, lactic acid can be obtained in high yield from cellulose-based plant biomass without sterilization. Moreover, according to the present invention, expensive and complex steps such as conventional steam sterilization can be omitted, which makes it possible to lower the cost of lactic acid production.

EMBODIMENTS FOR CARRYING OUT THE INVENTION

Figure 1:
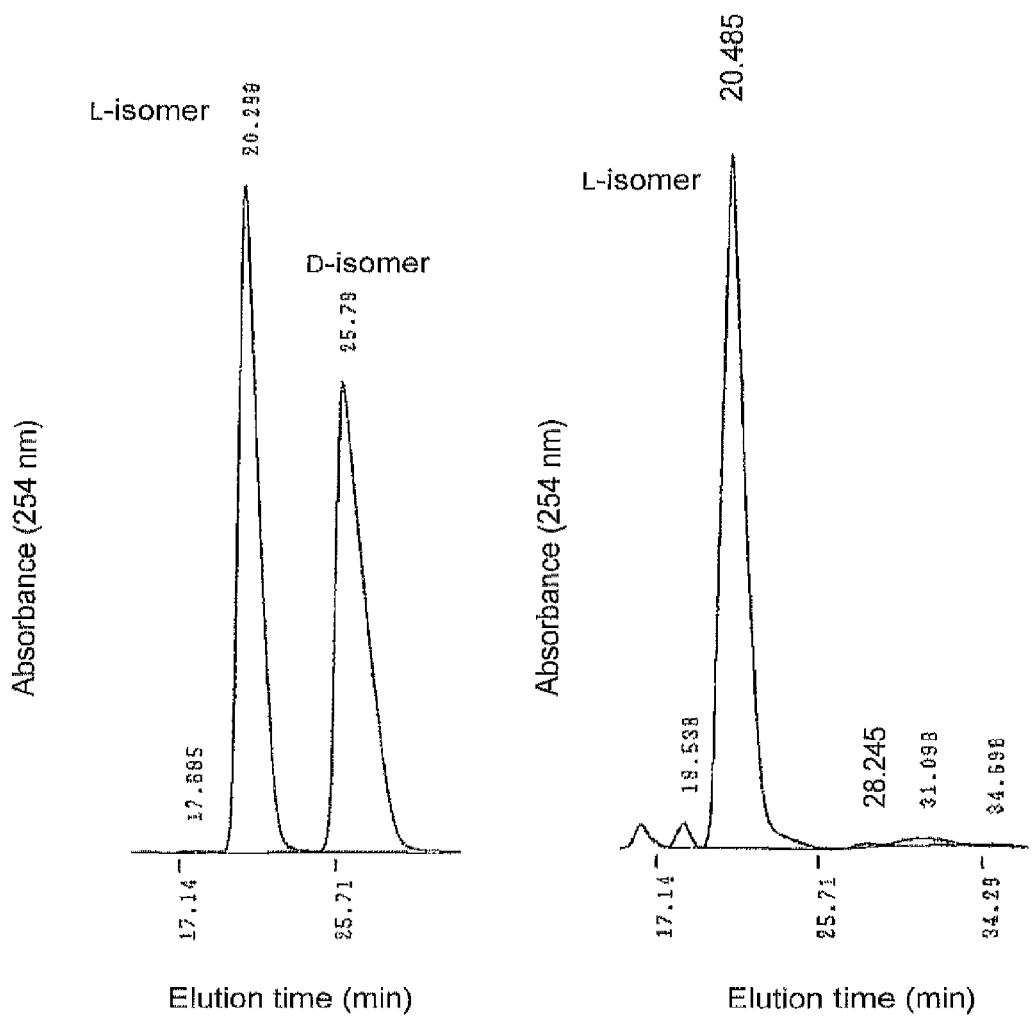
FIG. 1 shows the results of HPLC analysis, indicating optical purities of lactic acid produced in culture solutions of the strain L-120.

Hereafter, the present invention will be described in detail.
The lactic acid bacterium according to the present invention is an alkaliphilic lactic acid bacterium belonging to the genus *Enterococcus*, having a 16S ribosomal RNA (rRNA) gene that consists of the nucleotide sequence represented by SEQ ID NO: 1 or has 95% or more (preferably 96% or more, 97% or more, 98% or more, 99% or more, and most preferably 100%) homology with the nucleotide sequence represented by SEQ ID NO: 1. Here, the term "alkaliphilic lactic acid bacterium" refers to a lactic acid bacterium that can grow under alkaline conditions of pH 9 or higher pH (and preferably, pH 10 or more), for example. There are only a few microorganisms (saprophytic bacteria) capable of growing under alkaline conditions of about pH 10. Therefore, with the use of the lactic acid bacterium according to the present invention, which grows under alkaline conditions, a glycosylation solution containing glucose and xylose derived from plant biomass can be used for lactic fermentation (and particularly, lactic fermentation under alkaline conditions) without sterilization.

Sequence homology can be determined using DNA sequence analysis software such as programs listed at the website (blast.ddbj.nig.ac.jp/top-j.html) of DNA Data Bank of Japan (DDBJ) or ClustalX, for example.

Examples of the lactic acid bacterium according to the present invention include a lactic acid bacterium, that is *Enterococcus casseliflavus* (*E. casseliflavus*), and has the above properties and particularly the *E. casseliflavus* strain L-120 (hereinafter, referred to as the "strain L-120"). Also, a mutant strain of the above lactic acid bacterium, which is obtained by natural or artificial mutation (i.e., mutated by artificial means), grows under alkaline conditions, and performs lactic fermentation, is included among the examples of the lactic acid bacterium according to the present invention.

An example of a method for isolation of a lactic acid bacterium according to the present invention involves adding a sample derived from nature, such as from a drain outlet, soil, or plants, to a culture solution (medium) containing 10% glucose, 1% yeast extract, and 100 mM carbonate buffer (pH 10), and then isolating bacteria capable of growing well under non-aerated conditions as the lactic acid bacteria according to the present invention. The strain L-120 could be isolated according to this method.

The mycological properties of the thus isolated strain L-120 are as described below.

[Morphological Properties]
(1) Gram staining: positive
(2) Spores: None
(3) Motility: None
(4) Morphology: coccus

[Culture Properties]
The color tone of the colonies is semitransparent white. The colony is shaped like a small circle. The colony surface is smooth. Upon liquid culture, the strain produces a yellow pigment at the late stage of culture.

[Physiological Properties]
The viable pH ranges from 5 to 12 (the optimum growth pH ranges from 6 to 9; even at pH 10, the strain exhibits at least 50% of its growth rate at pH 7). Furthermore, the growth temperature ranges from 25° C. to 46° C. (and the optimum growth temperature ranges from 35° C. to 40° C.).

[Chemotaxonomical Properties]
DNA was extracted from the strain L-120, the 16S rRNA gene was amplified by PCR, the nucleotide sequence (SEQ ID NO: 1) of the thus amplified 16S rRNA gene was analyzed with an autosequencer, and then nucleotide sequences analogous to the analyzed sequence were examined by blast search.

As a result, the 16S rRNA gene of the strain L-120 was found to have homology as high as 99.9% (among 1245 bases, 1244 bases matched) with *E. casseliflavus*.

As described above, it was determined that the strain L-120 is a novel strain of *E. casseliflavus*.

It has been reported that *E. casseliflavus* (IFO 12256 strain) generates lactic acid with a yield of 78% using glucose as a substrate, and the optical purity of such L-lactic acid is 99% (Taniguchi, M., T. Tokunaga, K. Horiuchi, K. Hoshino, K. Sakai, T. Tanaka (2004) Production of L-lactic acid from a mixture of xylose and glucose by co-cultivation of lactic acid bacteria. Appl. Microbiol. Biotechnol. 66: 160-165). Furthermore, the growth of *E. casseliflavus* at pH 9.6 has been conventionally reported, but no growth thereof at pH 10 has been reported (Ludwig, W., Schleifer, K.-H., Whtman W. B. In P. De Vos et al. eds, Bwegey's Manual of Systematic Bacteriology Second edition Vol. 3 The Frimicutes. Springer, Dordrecht, Heidelberg, London, New York, pp. 594-607). Furthermore, other documents (including the above Bwegey's Manual of Systematic Bacteriology) do not describe the growth of the bacteria of the genus *Enterococcus* and the production of lactic acid by the bacteria at pH 10 or more.

Meanwhile, in the case of the strain L-120 described in the Examples below, the optical purity of L-lactic acid (obtained with a lactic acid yield of 96% to 100% with respect to glucose) is 100% and good growth at pH 10 (growth could be clearly observed within 24 hours of culture) is exhibited. Thus, the lactic acid bacterium of the present invention was confirmed to clearly have advantages in terms of usefulness in lactic acid production over conventionally known *E. casseliflavus* or other bacteria of the genus *Enterococcus*.

The strain L-120 was deposited on Sep. 14, 2009 at the International Patent Organism Depositary of the National Institute of Advanced Industrial Science and Technology (Central 6, 1-1-1 Higashi, Tsukuba, Ibaraki, Japan) under accession No. FERM P-21847 and then further transferred on Sep. 8, 2010 to the international deposit under accession No. FERM BP-11295.

The method for producing lactic acid according to the present invention comprises bringing the above lactic acid bacterium according to the present invention into contact with a cellulose glycosylation solution under pH conditions ranging from pH 5 to pH 11, for example, regardless of the presence or the absence of sterilization, culturing the bacterium, and thus performing lactic fermentation. In particular, the method for producing lactic acid according to the present invention can be performed under non-sterile condition. For example, in the method for producing lactic acid according to the present invention, the lactic acid bacterium according to the present invention is cultured in a medium containing a cellulose glycosylation solution under non-sterile and alkaline conditions (pH 9 to pH 11 and preferably pH 10 to pH 11), and after the proliferation thereof, bacteria are then further cultured under pH conditions ranging from pH 5 to pH 9 (preferably, pH 7) for lactic fermentation, so that lactic acid can be produced. Here, the term "under non-sterile condition" means that no sterilization is performed throughout the steps of the method for producing lactic acid according to the present invention. In particular, a cellulose glycosylation solution (medium) as a raw material generally needs to be sterilized. However, in the present invention, since microorganisms (saprophytic bacteria) capable of growing under alkaline conditions (e.g., about pH 10) are few and the lactic acid bacterium according to the present invention can grow under such alkaline conditions, a cellulose glycosylation solution can be used for culture and lactic fermentation (particularly, culture under alkaline conditions and lactic fermentation) without sterilization.

In the method for producing lactic acid according to the present invention, first the lactic acid bacterium according to the present invention and a cellulose glycosylation solution are prepared. A sufficient amount of the lactic acid bacterium according to the present invention to be inoculated can be prepared by culturing the lactic acid bacterium in a medium with the following composition (10% glucose, 1% yeast extract, and 100 mM carbonate buffer (pH 10)), for example, at a temperature between 25° C. and 45° C. (preferably between 30° C. and 37° C.) at a pH of 7 to 10 (preferably, pH 9 to 10) for a sufficient time period.

Meanwhile, regarding preparation of a cellulose glycosylation solution containing glucose, when lactic acid is generated with a yield of 100% from glucose, the ratio of the concentration of glucose to the concentration of lactic acid will be theoretically 1:1. This suggests that the concentration of lactic acid higher than the concentration of glucose added cannot be obtained. Also, the lactic acid purification process following lactic fermentation requires a high-concentration lactic acid solution. Moreover, lignin contained in plant biomass such as rice straw contains a fermentation inhibitor at a high concentration, and thus it should be removed before lactic fermentation.

Hence, the present inventors have found a method for generating high-concentration glucose from plant biomass. Specifically, lignin is removed by soaking plant biomass in an alkali solution, cellulose fiber is brought into contact with cellulase after removal of lignin, and thus a cellulose glycosylation solution containing glucose at a high concentration can be obtained. Examples of such an alkali solution to be used herein include a caustic soda (sodium hydroxide) solution, a potassium hydroxide solution, a sodium carbonate solution, and a calcium hydroxide solution. A preferred example thereof is a caustic soda solution.

Plant biomass contains a complex of the crystal structure of cellulose fiber and lignin, which is composed of cellulose, hemicellulose, lignin, and the like. Examples of plant biomass include herbaceous biomass and soft cellulose. Furthermore, examples of herbaceous biomass or soft cellulose include non-edible plant parts (nonfood cellulose-based plant biomass) such as rice straw and wheat straw, paper sludge, maize stem, strained lees of sugarcane, and rice hull. In particular, in the present invention, nonfood cellulose-based plant biomass from plants that are annual plants in terms of cultivation, such as rice straw or wheat straw, or maize stem is preferable.

For example, when plant biomass is rice straw, 1 L of 0.1 N to 2 N (preferably 0.2 N or more) alkali solution such as caustic soda is added per 50 g of rice straw, rice straw is soaked in the alkali solution, and then stirred well. Subsequently, the mixture is left to stand at room temperature for half a day or more (e.g., 1 day), or subjected to heat treatment at a high temperature that is 50° C. or higher (e.g., 50° C. to 120° C.) for 10 minutes or more (e.g., 20 minutes). Lignin is eluted in the solvent by this procedure. The thus obtained cellulose fiber is washed sufficiently with water, pH is adjusted at 2 to 6. The resultant is compressed and then dehydrated.

Subsequently, 200 ml of water is added per 50 g of the thus obtained wet cellulose, cellulase is added, and then reaction is allowed to proceed at 25° C. to 70° C. (e.g., 37° C.) for 2 or more hours (e.g., 10 hours). Examples of cellulase to be used herein include commercially available cellulase for biomass such as Cellic CTec (Novozymes) and *Trichoderma reesei*-derived cellulase. The amount of cellulase to be added to wet cellulose ranges from 500 EGU to 3,000 EGU (Endo Glucanase Unit) and preferably ranges from 2,000 EGU to 3,000 EGU per 50 g of wet cellulose, for example. In addition, further addition of xylanase (e.g., Cellic HTec (Novozymes)) having β-glucanase activity can accelerate glycosylation. The amount of xylanase to be added to wet cellulose ranges from 500 FXU to 3,000 FXU (Farvet Xylan Unit) and preferably ranges from 2,000 FXU to 3,000 FXU per 50 g of wet cellulose.

After reaction of wet cellulose with cellulase (or a combination of cellulase with xylanase), wet cellulose is further added to the reaction solution for reaction. This is repeated several times (e.g., 5 times), so that a high-concentration glucose solution can be obtained. The thus obtained cellulose glycosylation solution (glucose) can be used as a cellulose glycosylation solution to be used in the method for producing lactic acid according to the present invention, or a composition (medium) for lactic fermentation. In addition, as a nitrogen source, 30 g of bean curd refuse or 5 g of yeast extract is preferably added per 500 ml of 150 g/L glucose-containing cellulose glycosylation solution, for example. Furthermore, vitamins and a mineral source; that is a degradation product of bran (e.g., 1.5% by weight with respect to the whole medium) obtained by cellulase hydrolysis, and fish food-derived peptone; that is a nitrogen source (e.g., 0.3% by weight with respect to the whole medium) can be added as lactic fermentation-accelerating substances.

With the method for producing lactic acid according to the present invention, the prepared lactic acid bacterium according to the present invention is inoculated in a medium containing a cellulose glycosylation solution and then cultured without sterilization, so that lactic fermentation can be performed. Specifically, the lactic acid bacterium according to the present invention is inoculated at 0.01 g or more of wet cells (preferably 0.05 g or inure of wet cells) per 100 g of glucose in a cellulose glycosylation solution, for example. Cells are cultured at a pH of 9 to 11 (e.g., pH 9 or higher, preferably pH 10 or more) and a temperature between 20° C. and 40° C. (e.g., 30° C.) for 12 to 24 hours (e.g., 24 hours). Thereafter, cells are further cultured at a pH of 5 to 9 (preferably pH 7) for 1 to 5 days (preferably 3 days), so that lactic fermentation is performed. High-concentration (e.g., 12% (w/v) in the culture solution) of L-lactic acid having optical purity as high as 95% or inure can be obtained by the lactic fermentation. Also, with the use of the lactic acid bacterium according to the present invention, lactic acid can also be produced from xylose obtained by glycosylation of cellulose-based biomass. Therefore, a cellulose glycosylation solution may contain not only glucose, but also xylose.

Alternatively, regardless of the presence or the absence of sterilization, the lactic acid bacterium according to the present invention is inoculated in a medium containing a cellulose glycosylation solution, and culture and lactic fermentation are then performed under about neutral pH conditions (e.g., pH 6 to pH 8, preferably pH 7), so that high-concentration of lactic acid can also be obtained.

After culture, a culture solution recovered by centrifugation or the like from the cells can be directly used as lactic acid, or further subjected to a general purification means or extraction means, so that lactic acid can be purified and/or extracted.

EXAMPLES

The present invention will be hereafter described in detail with reference to the following examples, although the technical scope of the present invention is not limited thereto.

Example 1

Isolation of Alkaliphilic Lactic Acid Bacterium

Water stain at a drain outlet was added to a culture solution containing 10% glucose, 1% yeast extract, and 100 mM carbonate buffer (pH 10). The bacterium that had grown well under anaerobic conditions was isolated and termed the strain L-120. Specific isolation method of bacterium is as follows. Culture was performed under anaerobic conditions while maintaining a rice straw glycosylation solution that had been delignified (described later) at pH 10 using a pH controller. Bacteria spontaneously grown under anaerobic conditions of no sterilization, substitution of air with nitrogen, and pH 10 maintained using the pH controller were isolated. The strain L-120 obtained through the above isolation process grew even when another bacterial strain had been seeded in a medium containing a rice straw glycosylation solution that had been delignified, as a substrate. Thus, the strain L-120 is thought to have very high compatibility with a medium containing such a rice straw glycosylation solution as a substrate.

Example 2

Lactic-Acid-Producing Nature of the Strain L-120 Under General Culture Conditions The strain L-120 was cultured in a medium containing glucose (16.2 wt %) (containing glucose resulting from hydrolysis of bran), yeast extract (0.8 wt %), fish food-derived peptone (0.3 wt %), and a degraded product of bran (1.5 wt %) (degraded with cellulase (Amano Enzyme)) at pH 9 (maintained with a pH controller and 10 N NaOH), at 35° C. under anaerobic conditions. After 67 hours of culture, 16.9 wt % lactic acid per 1 L was obtained, and thus the recovery of lactic acid was about 100% with respect to glucose added to the medium.

The optical purity of the thus obtained lactic acid was measured by high performance liquid chromatography (HPLC) using a SUMICHIRAL OA-500 column (4.6 mm×150 mm) and 1 mM copper sulfate as liquid phase. The results are shown in FIG. 1. In FIG. 1, the left panel shows HPLC analytical results for standard lactic acid containing 50% L-isomer and 50% D-isomer. The right panel shows HPLC analytical results for L-lactic acid produced by the strain L-120. As shown in FIG. 1, since no peak was observed at 25.71 minutes (at which time the peak of D-lactic acid appeared), the strain L-120 produced only L-isomer of lactic acid (100%).

Example 3

Glycosylation of Rice Straw Cellulose

1 L of 1 N caustic soda was added per 50 g of rice straw cut to a length of about 10 cm or less, followed by 20 minutes of heating at 120° C.

Water (50 ml) and commercially available cellulase and xylanase (Novozymes: 0.2 ml of Cellic CTec and 0.2 ml of Cellic HTec (corresponding to 200 EGU and 200 FXU, respectively)) were added per 10 g of the thus obtained delignified rice straw so that reaction could proceed at 37° C. for 1 day. After reaction, 10 g of delignified rice straw was further added so that reaction could proceed for 1 day. This procedure was repeated. The amount of sugar (glucose) in the reaction product (glycosylation solution) was measured by a DNS (3,5-dinitro salicylic acid) method. The results are shown in FIG. 2.

Figure 2:
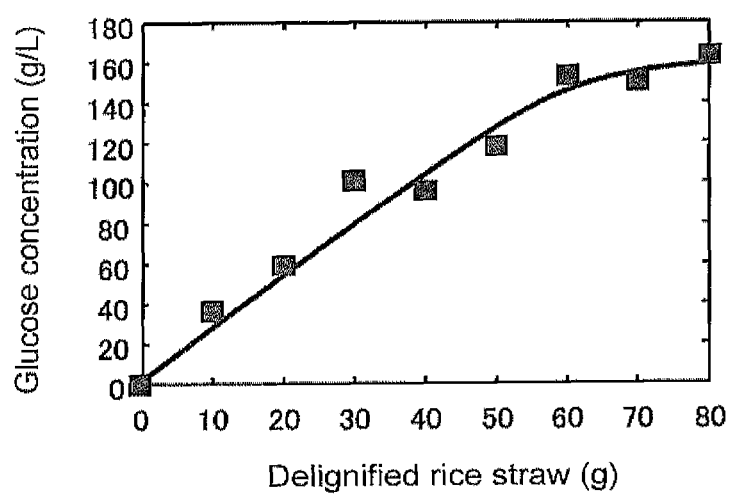
FIG. 2 is a graph showing the relationship between amounts of delignified rice straw added and concentrations (g/L) of the thus generated sugar (glucose).

FIG. 2 shows the amounts of delignified rice straw added and the concentrations (g/L) of sugar (glucose) generated by cellulase and xylanase. As shown in FIG. 2, 160 g/L sugar (glucose) was detected in the glycosylation solution obtained via addition of a total of 80 g of delignified rice straw.

Example 4

Lactic Fermentation 1 Using the Strain L-120 Under Alkaline Conditions

1 L of 1 N caustic soda was added per 50 g of rice straw cut to a length of about 10 cm or less and then the mixture was heated at 120° C. for 20 minutes. After cooling, cellulose filtered with gauze was sufficiently washed with water and then squeezed to sufficiently remove the water, so that wet cellulose was obtained. In this manner, 100 g of wet cellulose was obtained per 50 g of rice straw.

200 ml of water was added per 50 g of the thus obtained wet cellulose, and pH was adjusted to about 2 to 6. Cellulases for biomass; that is, 1.5 ml of Cellic CTec, and 1.5 ml of xylanase Cellic HTec (both produced by Novozymes) were added (corresponding to 1500 EGU and 1500 FXU, respectively) so that reaction could proceed at 37° C. for 12 hours, and thus glycosylation was performed. The above wet cellulose (50 g), 1.5 ml of the above cellulase, and 1.5 ml of the above xylanase were added to the thus obtained glycosylation solution so that reaction could proceed at 37° C. for 12 hours. Through repetition of the addition of 50 g of the wet cellulose 4 times, 500 ml of a 150 g/L glucose solution (glycosylation solution) was prepared.

30 g of bean curd refuse was added per 500 ml of the thus obtained glucose solution, pH was adjusted to 10, and then 10 ml of the overnight culture solution (0.1 g of wet cells) of the strain L-120 was inoculated without sterilization. The culture product was cultured without aeration at 30° C. for 1 day, and then the culture solution was adjusted to pH 7, followed by 2 days of culture.

Table 1 shows lactic acid concentrations (w/v %) in the culture solution obtained by the above culture (lactic fermentation) after different numbers of days for culture.

TABLE 1

|  | Days for culture (day) | | |
| --- | --- | --- | --- |
|  | 1 | 2 | 3 |
| Lactic acid concentration (w/v %) | 8.9 | 11 | 12 |

As shown in Table 1, 12% (w/v) lactic acid was obtained by 3 days of culture.

Example 5

Lactic Fermentation 2 Using the Strain L-120 Under Neutral Conditions

The strain L-120 (0.1 g of wet cells) was inoculated to a medium containing glucose (20%) (w/v) and yeast extract (5%) (w/v) without sterilization, and then cells were cultured for 3 days under neutral conditions (pH7) at 30° C. After 3 days of culture, 17% (w/v) lactic acid was obtained in the thus obtained culture solution. Furthermore, even when sterilization was performed, similar high-concentration of lactic acid could be obtained.

Example 6

Xylose Metabolism by the Strain L-120

When cellulose-based biomass is glycosylated, xylose accounts for about 20% of all the reducing sugars. The use of xylose is essential for the effective use of cellulose-based biomass. However, it is significantly more difficult to use xylose than glucose. For example, most types of yeast are unable to use xylose.

Figure 3:
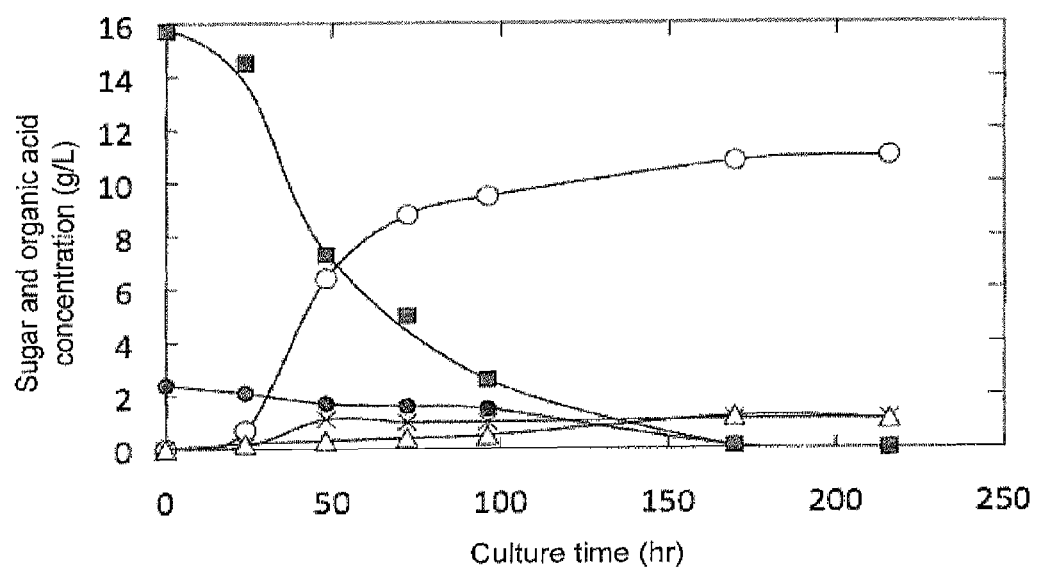
FIG. 3 is a graph showing xylose metabolism by the strain L-120.

FIG. 3 shows the concentrations of organic acid generated by the strain L-120 using media (containing 5 wt % yeast extract) containing 16 wt % glucose and 2.4 wt % xylose as carbon sources. In FIG. 3, each graph shows the concentrations of the following sugars and organic acids.

Graph with black square marks: glucose concentration
Graph with black circular marks: xylose concentration
Graph with white circular marks: lactic acid concentration
Graph with white triangle marks: acetic acid concentration
Graph with "x" marks: formic acid concentration The strain L-120 was cultured for 20 hours in the medium without any aeration until starter bacteria grew sufficiently while the growth of saprophytic bacteria was suppressed at pH 9. Subsequently, the strain L-120 was cultured for 8 days at or below pH 7.5, at which productivity of lactic acid was high so as to allow easy metabolization of xylose. As a result, as shown in FIG. 3, 11 wt % lactic acid was obtained and the concentration of the remaining xylose was 0.2 wt %.

Thus, the strain L-120 has characteristics appropriate for lactic acid production from a glycosylation solution of cellulose-based biomass, such that it is capable of metabolizing not only glucose, but also xylose for lactic fermentation.

Example 7

Search for Lactic-Fermentation-Accelerating Substance

Lactic fermentation requires the addition of a nitrogen source, various vitamins, and minerals, as well as glucose. A yeast extract is generally added for the addition of these nutrients, but this results in high cost. Hence, a substance that could serve as an alternative therefor was searched for.

Figure 4:
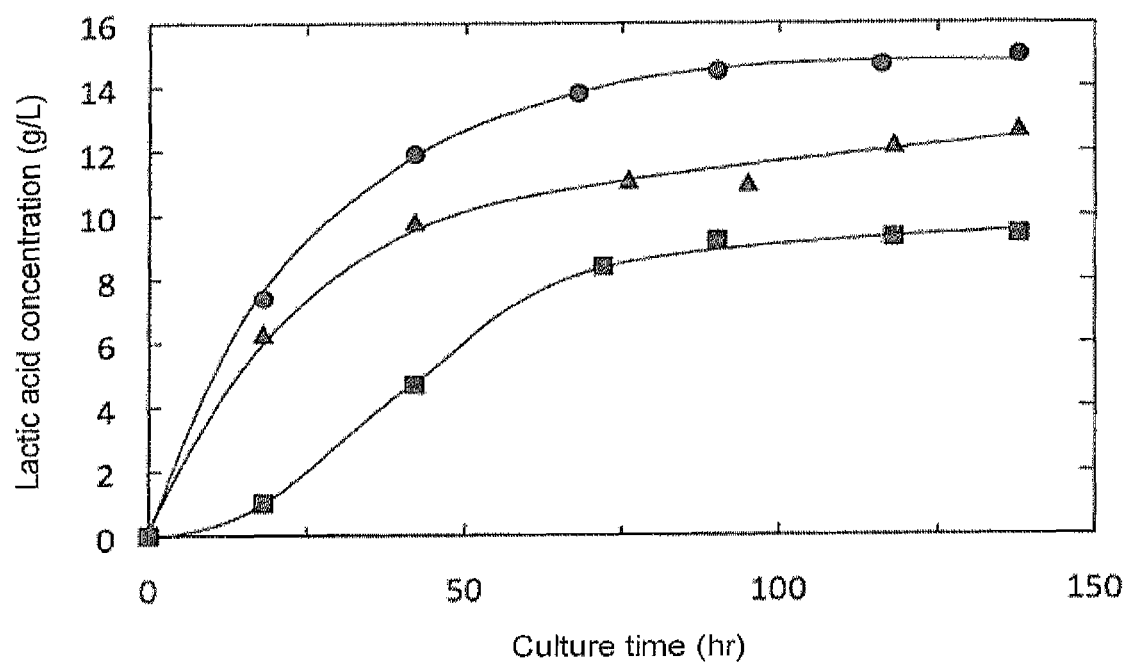
FIG. 4 is a graph showing lactic acid generation by the strain L-120 in the presence of lactic-fermentation-accelerating substances.

The results are shown in FIG. 4. FIG. 4 shows the concentrations (g/L) of lactic acid generated: when the strain L-120 was cultured in a medium containing glucose (18 wt %), yeast extract (0.8 wt %), and fish food-derived peptone (0.3 wt %) at pH 9 and 27° C. (graph with black square marks) or 35° C. (graph shown with black triangle marks); or when a degraded product of bran (1.5 wt %) was further added to the medium, following which the strain L-120 was cultured at pH 9 and 35° C. in the medium containing the degraded product of bran (graph with black circular marks).

As shown in FIG. 4, the lactic acid productivity of the strain L-120 could be improved by adding bran hydrolyzed with cellulase as vitamins and a mineral source, and fish-food-derived peptone as a nitrogen source. Furthermore, lactic acid generation rate can be improved by maintaining the culture temperature at 35° C. Lactic acid (15 wt %) could be obtained by culturing the strain L-120 at 35° C. for 6 days in a medium adjusted to pH 9 containing 18 wt % glucose, 1.5 wt % degraded product of bran, and 0.3 wt % fish food peptone (the graph with black circular marks in FIG. 4).

INDUSTRIAL APPLICABILITY

According to the present invention, a medium appropriate for lactic fermentation can be prepared from nonfood plant biomass such as rice straw, so that a raw material for producing lactic acid can be obtained inexpensively without competing with foods. Also, lactic acid production according to the present invention does not require high-temperature, high-pressure sterilization, so that drastic simplification of lactic fermentation apparatuses becomes possible.

Accession Number

FERM BP-11295

All publications, patents, and patent applications cited herein are incorporated herein by reference in their entirety.

The invention claimed is:

1. An isolated alkaliphilic lactic acid bacterium belonging to the genus *Enterococcus casseliflavus*, which grows under alkaline conditions of pH 10 or more, wherein said bacterium is the *Enterococcus casseliflavus* L-120 strain that has been deposited under accession No. FERM BP-11295.

2. A method for producing lactic acid comprising a step of culturing the isolated alkaliphilic lactic acid bacterium according to claim 1 under non-sterile condition and at a pH of 9 to 11 in a medium containing a cellulose glycosylation solution and further culturing the bacterium at a pH of 5 to 9.

3. The method according to claim 2, wherein the cellulose glycosylation solution is obtained from a non-edible plant part.

4. The method according to claim 3, wherein the non-edible plant part is rice straw, wheat straw, or maize stem.

5. The method according to claim 2 further comprising a step of soaking plant biomass in an alkali solution to remove lignin and a step of bringing cellulose fiber into contact with cellulase to obtain a cellulose glycosylation solution.

6. The method according to claim 5, wherein the alkali solution is a caustic soda solution.

7. The method according to claim 5 comprising leaving the soaked plant biomass at room temperature or subjecting the soaked plant biomass to heat treatment.

* * * * *